(12) United States Patent
Burke et al.

(10) Patent No.: US 10,238,524 B2
(45) Date of Patent: Mar. 26, 2019

(54) TIGHTENING SYSTEM FOR ORTHOTICS

(71) Applicant: ASPEN MEDICAL PARTNERS, LLC, Irvine, CA (US)

(72) Inventors: Steven Burke, Huntington Beach, CA (US); Jozsef Horvath, Fullerton, CA (US); Erik Zimmer, Oceanside, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 0 days.

(21) Appl. No.: 15/516,790

(22) PCT Filed: Apr. 19, 2016

(86) PCT No.: PCT/US2016/028252
§ 371 (c)(1),
(2) Date: Apr. 4, 2017

(87) PCT Pub. No.: WO2016/204859
PCT Pub. Date: Dec. 22, 2016

(65) Prior Publication Data
US 2018/0085243 A1     Mar. 29, 2018

Related U.S. Application Data (60) Provisional application No. 62/182,337, filed on Jun. 19, 2016.

(51) Int. Cl.
| A61F 5/00 | (2006.01) |
| A61F 5/02 | (2006.01) |
| A61F 5/048 | (2006.01) |

(52) U.S. Cl.
CPC ............ *A61F 5/028* (2013.01); *A61F 5/02* (2013.01); *A61F 5/048* (2013.01)

(58) Field of Classification Search
USPC .......................................................... 602/19
See application file for complete search history.

(56) References Cited

U.S. PATENT DOCUMENTS

| 5,346,461 | A | 8/1994 | Heinz et al. |
| 5,437,617 | A | 8/1995 | Heinz |
| RE35,940 | E | 10/1998 | Heinz et al. |
| 6,190,343 | B1 | 2/2001 | Heinz et al. |
| 6,213,968 | B1 | 4/2001 | Heinz |
| 6,503,215 | B1 | 1/2003 | Reinhardt et al. |
| 6,517,502 | B2 | 2/2003 | Heyman et al. |
| 6,602,214 | B2 | 8/2003 | Heinz et al. |
| 7,001,348 | B2 | 2/2006 | Garth et al. |
| 7,135,005 | B2 | 11/2006 | Kania |
| 8,372,023 | B2 | 2/2013 | Garth et al. |
| 8,556,840 | B2 | 10/2013 | Burke |

(Continued)

FOREIGN PATENT DOCUMENTS

| CN | 2464870 | 12/2001 |
| EP | 0732905 B1 | 9/2000 |

*Primary Examiner* — Kim M Lewis
(74) *Attorney, Agent, or Firm* — Fish IP Law, LLP (57) ABSTRACT

Tightening systems for braces and other objects are provided. One or more housings can be provided, each of which includes a top surface, a set of lobes positioned on and along the top surface, and a set of sheaves that are sized and dimensioned to be rotatably secured between the top surface and the set of lobes.

24 Claims, 5 Drawing Sheets

(56) References Cited

U.S. PATENT DOCUMENTS

| | | |
|---|---|---|
| 8,926,537 B2 | 1/2015 | Ingimundarson |
| 2001/0020144 A1 | 9/2001 | Heinz et al. |
| 2001/0034498 A1 | 10/2001 | Heyman et al. |
| 2002/0100900 A1 | 8/2002 | Graham |
| 2005/0273025 A1 | 12/2005 | Houser |
| 2006/0004313 A1 | 1/2006 | Heinz et al. |
| 2008/0066272 A1 | 3/2008 | Hammerslag et al. |
| 2009/0082707 A1 | 3/2009 | Rumsey |
| 2010/0268141 A1* | 10/2010 | Bannister ............... A61F 5/028 602/19 |
| 2013/0237891 A1 | 9/2013 | Fryman et al. |
| 2014/0364786 A1 | 12/2014 | Haider et al. |
| 2015/0014463 A1 | 1/2015 | Converse et al. |
| 2015/0018739 A1 | 1/2015 | Threlfall |
| 2015/0032041 A1 | 1/2015 | Ingimundarson et al. |

* cited by examiner

TIGHTENING SYSTEM FOR ORTHOTICS

This application claims priority to U.S. provisional patent application Ser. No. 62/182,337 filed on Jun. 19, 2015. This and all other extrinsic references identified herein are incorporated by reference to the same extent as if each individual reference or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is tightening systems for orthotics.

BACKGROUND

The following description includes information that may be useful in understanding the present invention. It is not an admission that any of the information provided herein is prior art or relevant to the presently claimed invention, or that any publication specifically or implicitly referenced is prior art.

Various braces are known that utilize one or more cords to tighten a lumbar region of the braces. See, e.g., U.S. Pat. Nos. 8,372,023 and 7,001,348. These braces include a tightening system that utilizes pulleys and a cord with a pull tab to adjust a proper tension of a lumbar area of the brace. However, such systems can be overly complicated to manufacturer increasing the cost of the systems, and often fail to allow for the flexibility needed to comfortably use the tightening systems with different body types.

U.S. patent publication no. 2013/0237891 to Fryman teaches a stacked pulley housed in a pulley housing via pins; however, the stacked pulley is entirely enclosed in the housing. Furthermore, the housing and connection of Fryman's tightening system appears not to be sufficiently flexible, among other problems.

Thus, there is still a need for tightening systems having a lower cost of manufacture and added comfort for a wearer.

SUMMARY

The inventive subject matter provides tightening systems for braces that include a set of lobes positioned along a surface of a housing, which are sized and dimensioned to securely and rotatably receive a set of cord guiding sheaves. The lobes and the surface could form a plurality of openings through which a sheave could be received. Where sheaves include one or more pins or protrusions, the opening could include one or more notches that are sized and dimensioned to receive the pins. Viewed from a different perspective, the lobes and the top surface could include one or more recessed paths that are configured to guide the pins to a position between the lobe and the top surface.

In some aspects, a lobe can be a single continuous piece that includes (a) an open side or opening sized and dimensioned to receive a thickness and a central length of a sheave, and (b) a closed side that acts as a blocking member to prevent a movement of the sheave in at least one direction. In such embodiments, it is preferred that the lobe includes at least one through-hole for a cord to pass through when engaging the sheave.

In some other aspects, the lobe can comprise two or more pieces. The first piece can be sized and dimensioned such that the thickness and a central length of the sheave can be positioned between the top surface of the housing and the first piece. The second piece can comprise the blocking member, and be positioned adjacent the first piece to form one or more gaps. The gap(s) will preferably be sized and dimensioned to both receive and secure a pin of the sheave, and allow a cord to pass through the lobe when engaging the sheave. In some preferred embodiments, the sheaves can freely rotate in its place within a lobe when a cord that engages the sheaves is pulled on or retracted.

The housing surfaces can include thinner and thicker regions that provide for varying flexibility along a length or width. The thinner regions can be recessed relative to the thicker regions, and can be used to sew the housing to a brace or other object. Additionally or alternatively, the thinner regions can include recessed paths through which a sheave's pins can pass. The inner surface of the lobe can include a raised path opposite a recessed path, and the two paths can be sized and dimensioned to allow the pins of a sheave to pass between the top surface and the lobe. The sheaves may be removable from a position between the top surface and the respective lobe with force. Alternatively, the sheaves may not be removable (without damage or breakage) from its respective lobe once inserted and secured.

The inventive subject matter also provides lower back and other braces that are adjustable via a tightening system. In some aspects, a lower back brace includes a belt configured to wrap at least partially around a mid-portion of a wearer. The belt could be made from one or more pieces of material, and two housings could be secured to the same or separate pieces of the belt. Each of the housings will preferably include a top and bottom surface, and have a varying thickness. A set of lobes could be positioned along the top surface of the housings, and form a plurality of openings that are sized and dimensioned to receive a plurality of cord guiding sheaves. Where the sheaves include one or more pin portions, the opening could include one or more notches that are sized and dimensioned to receive the pin portions. Viewed from a different perspective, the lobes and the top surface could include one or more recessed paths that are configured to guide the pin portions to a position between the lobe and the top surface.

One or more cords could sinuously engage the sheaves of the two housings, crossing the lower back of a wearer. The cords could separately be coupled with one or more pull tabs, which could each include a fastener (e.g., hook fastener) configured to releasably couple with different portions of the belt. When the brace is worn, the wearer could pull on the pull tabs to adjust the tightness of the belt by adjusting the distance between the first and second housings. When a desired tightness is achieved, the pull tabs could be attached to the belt via the fasteners.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

FIGS. 1A-3E illustrate numerous views of a tightening system for orthotics and other apparatuses. The tightening system includes housing 100A having two ends 106A and 106B. A plurality of lobes 112A, 112B, 112C including blocks 116A, 116B, 116C are positioned on a top surface of housing 100A between ends 106A and 106B, and configured to securely receive cord guiding sheaves 110A, 110B, 110C.

Figures 1A, 1B:
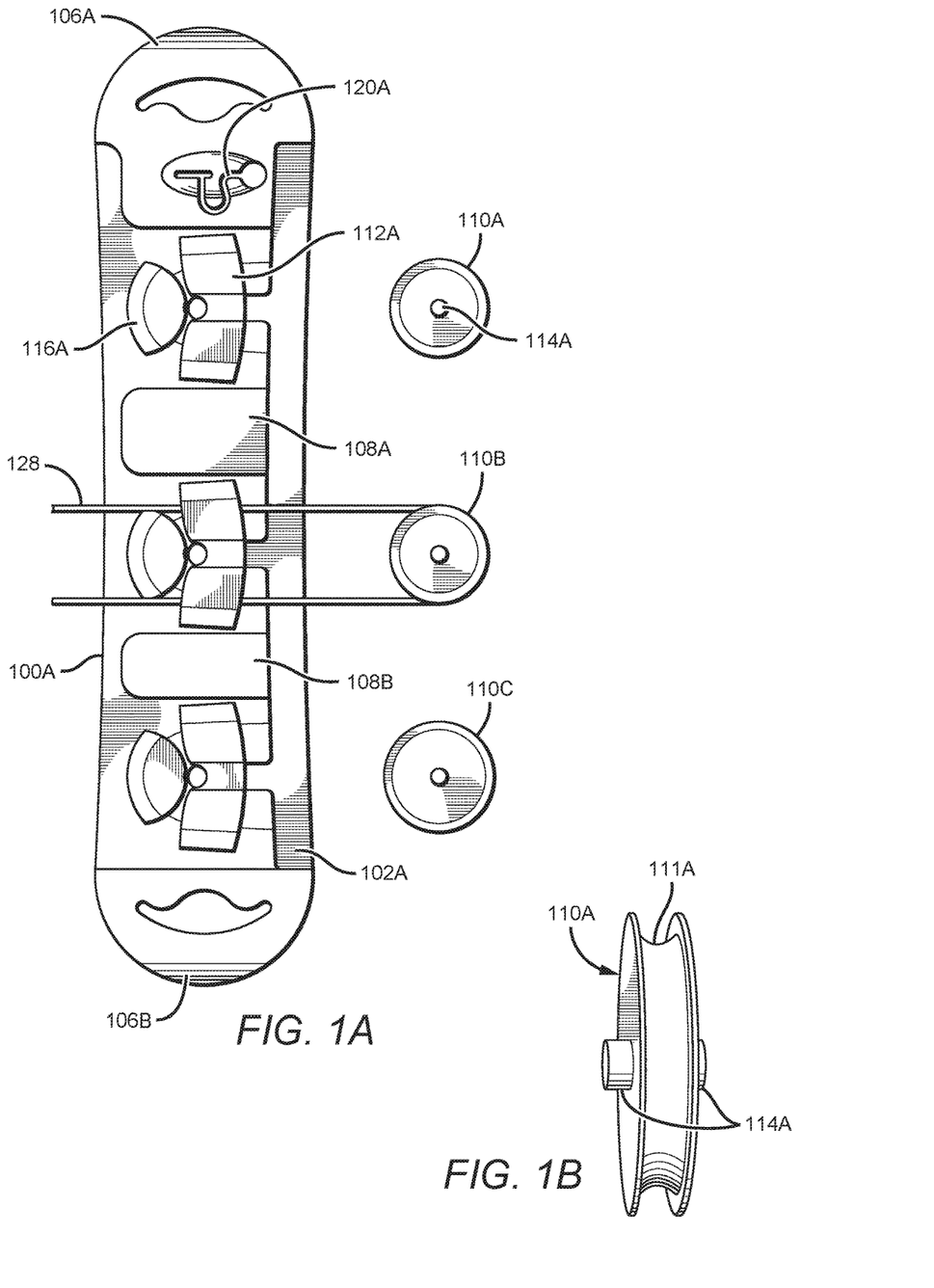
FIG. 1A is a top view of a tightening system of the inventive subject matter with sheaves removed from a housing.
FIG. 1B is a side perspective view of a sheave.

FIG. 1A illustrates a top view of the top surface of the tightening system. Housing 100A is able to receive a set of sheaves 110A, 110B, 110C that can rotate with respect to the housing 100A when disposed at least partially between the lobes (e.g., 112A) and the top surface of the housing 100A.

The housing 100A preferably is composed of plastic, although any commercially suitable material(s) could be used including metals and metal composites and so forth. The specific material(s) is preferably chosen to allow the housing 100A sufficient flexibility to bend to fit to the lordosis of a back of the wearer of the orthotic comprising the housing 100A. The housing 100A's top surface can advantageously include areas of increased thickness disposed between the lobes (e.g., 112A). As used here, the term "thickness" means the distance between the top and bottom surfaces of the housing 100A.

Each of the sheaves 110A, 110B, 110C is sized and dimensioned to be received between a lobe (e.g., 112A) and the top surface of the housing through an opening. In some preferred embodiments, the lobes are integral with the housing 100A's top surface, and the bottom surface is substantially planar (e.g., at least 50% planar, at least 70% planar, at least 80% planar, at least 90% planar) and lacks projections. A smooth bottom surface advantageously allows the tightening system to be used on braces and other worn objects without discomfort.

A pin 114A on top and bottom portions of the sheave 110A locks the sheave into housing 100A between the lobe 112A and the top surface. Viewed from another perspective, sheave 110A could comprise a first pin or pin portion that extends from a first wall (top wall) of the sheave, and a second pin or pin portion that extends from a second wall (bottom wall) of the sheave. The first and second walls can define a cord receiving portion 111A.

In preferred embodiments, the pin 114A or pin portions extending from top and bottom portions (or first and second walls) of the sheave has a height as measured from its maximum vertical distance from the top and bottom portions that is less than a width of the body of the sheave itself. As some non-limiting examples, a distance from an outer surface of the first wall and an outer surface of the second wall can be less than 15 mm, less than 10 mm, less than 5 mm, between 5-10 mm, or even less than 5 mm, and pin 114A can extend out from the first wall to a distance or height of less than 10 mm, less than 5 mm, less than 3 mm, between 3-10 mm, between 3-8 mm, or between 3-5 mm.

Each of the sheaves 110A, 110B, 110C may be removable from the respective lobe (e.g., 112A) with force, although is preferred embodiments, each sheave is not removable (without a tool, damage or breakage) from its respective lobe once inserted and secured.

Figure 4:
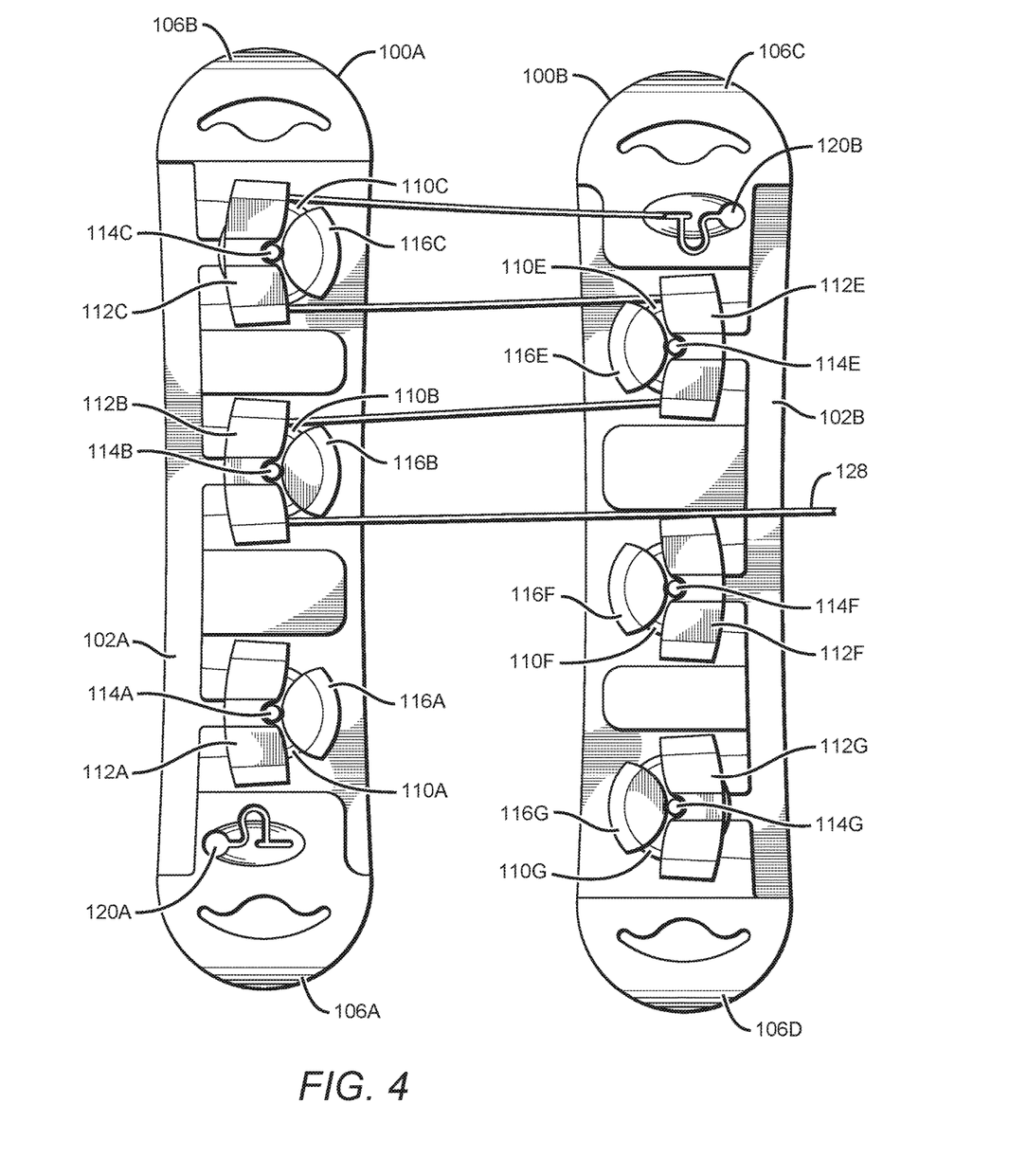
FIG. 4 illustrates a top view of a tightening system including two housings and a cord.

In the tightening system shown, housing 100A comprises three lobes, each of which can receive a sheave. Of course, the number of lobes can vary depending on the application. The three lobes/sheaves shown provide for a 4:1 mechanical advantage when two opposing housings are connected by a pull string, such as shown in FIG. 4. However, a range of possible configurations are possible from having a mechanical advantage of 1:1 and greater.

The housing 100A has a number of innovative features that differentiates it from tightening systems known in the art. For example, a surface of the housing 100A (described here the top portion or top surface) comprises a thinned area 102A or recessed portion along its length that has an overall height that is less than a normal height of the housing 100A. This advantageously allows for the housing 100A to be attached to a fabric brace or other orthotic, for example, by sewing or the use of other fasteners. A thinned area could additionally or alternatively be on a bottom surface of the housing.

Viewed from another perspective, the thinned portion could comprise any portion of the housing, and could extend along at least 50% of a length of the housing, the length being from end 106A to 106B. Additionally or alternatively, the thinned region could extend along an outer edge portion of the housing (e.g., at least 25% of an outer edge of the housing, at least 30% of an outer edge of the housing, at least 50% of an outer edge of the housing). Additionally or alternatively, the thinned portion could have a width that is between 5-20% of a width of the housing, between 10-20% of a width of the housing, at least 10% of a width of the housing, at least 15% of a width of the housing, or any other suitable width.

The thinned area 102A or other portion of the housing preferably can include a recessed path 104A (see FIG. 2B) that leads to an opening of a corresponding lobe 112A along which the sheave 110A can be inserted into the lobe 112A. The path could in some embodiments extend from an outer edge of the housing to a position beneath a lobe. In other embodiments, the path could extend from a non-edge portion of the housing to a position beneath the lobe, or between any other portions of the housing.

The configuration of the housing 100A including the placement and structure of the lobes (e.g., 112A) takes advantage of the assembly process and the direction of pull of the cord 128 that passes along the sheaves 110A, 110B, 110C to ensure the sheaves are securely confined to the housing 100A. Each lobe (e.g., 112A) preferably comprises a piece of plastic or other element (e.g., block element 116A) disposed on a side of the sheave 110A (i.e., in the direction of pull), which ensures that the sheave 110A is not unintentionally removed from the assembly and also acts to manage the pull cord to reduce the possibility of cords being tangled when slack is present in the assembly.

A lobe can be a single continuous piece that includes an open end sized and dimensioned to receive a diameter of a sheave, and a closed end that acts as the blocking member. In such embodiments, it is generally preferred that the lobe includes one or more through-holes for a cord to pass through, for example, two spaced apart holes. Two through-holes can be spaced apart by more than 1 cm, and are preferably aligned with opposite sides of a cord receiving portion (see FIG. 1B). Viewed from another perspective, the length of a line extending between the two apertures can be within 70%, within 80%, and most preferably within 90% of a diameter of the cord receiving portion.

As illustrated in FIG. 1B, sheave 110A includes a cord receiving portion 111A, which is sized and dimensioned to receive at least a portion of a cord. The element midline to the sheave 110A, pin 114A, acts to secure the sheave 110A within the lobe 112A (FIG. 1A) with a snap-in recess, and also acts to reduce or eliminate the bending of this part of the housing 100A (FIG. 1A). If the housing 100A is allowed to bend too much in this area, the sheave 110A may bind on the elements of the housing 100A causing the sheave 110A to stop rotating and possibly fail.

In the embodiments shown, the lobes (e.g., 112A) each comprise two pieces, wherein a first piece is sized and dimensioned to allow a diameter of a sheave to be positioned between the top surface and the first piece, and wherein a second piece comprises a blocking member. The blocking member is positioned adjacent to the first piece to form a gap that is sized and dimensioned to receive a pin 114A, and to allow cord 128 to pass (as better illustrated in FIG. 4). The blocking member advantageously prevents a movement of a sheave in at least one direction, preferably including a direction that the cord pulls on the sheave. A length of the blocking member can be within 70%, within 80%, and most preferably within 90% of a diameter of the cord receiving portion.

Figure 2A:
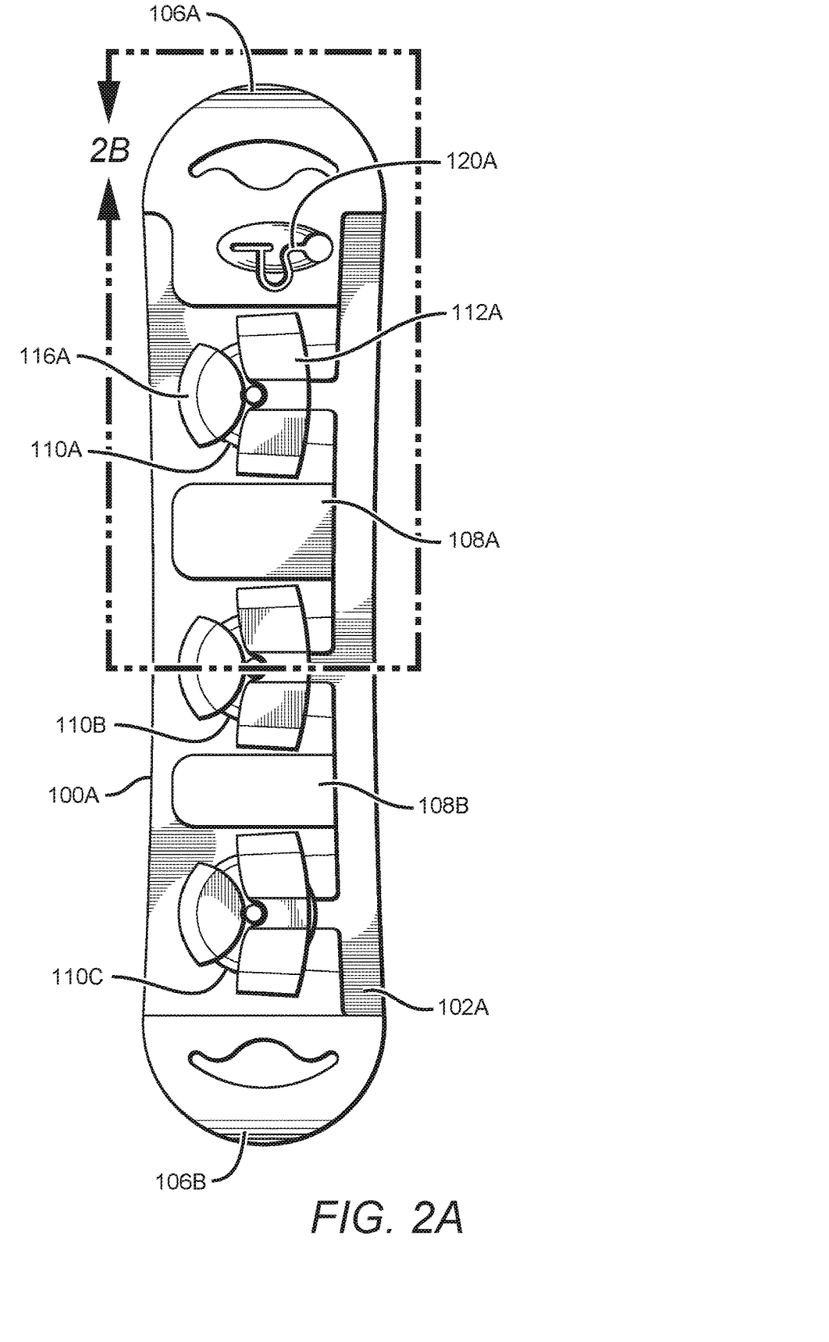
FIGS. 2A-2B are top views of a portion of the tightening system of FIG. 1A with sheaves inserted into the housing.
Figure 2B:
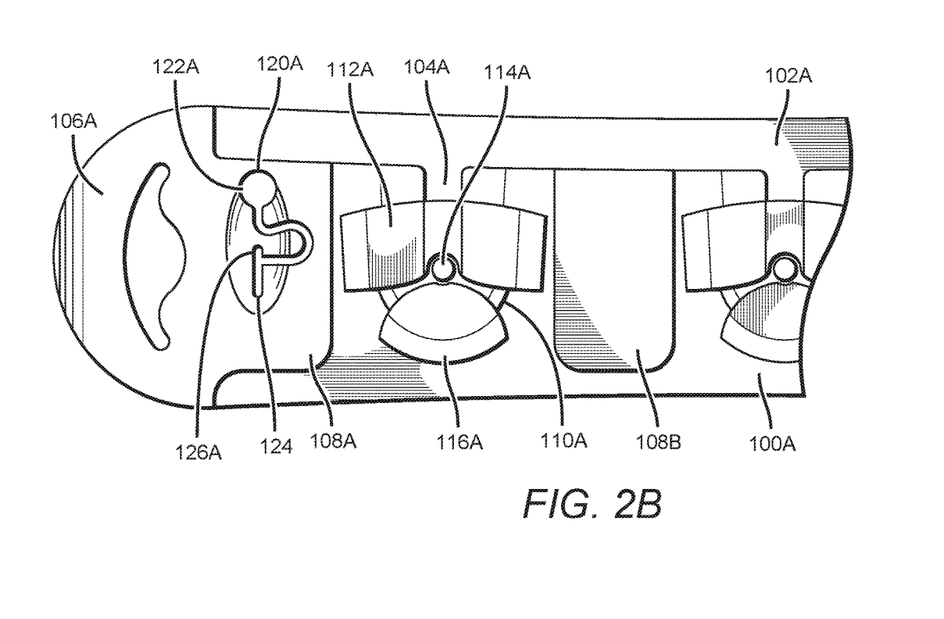

FIG. 2B provides an enlarged view of a portion of the tightening system of FIG. 1A as indicated by Box 2B in FIG. 2A. Unlike end 106B, which includes only a single through-hole that provides flexibility to housing 100A, end 106A additionally includes a cord retention device (or track) 120A for securing cord 128. Cord retention device 120A is configured to stop cord 128 from retracting beyond a specific point (where a block or knot on cord 128 meets cord retention device 120A.

Cord retention device 120A comprises an aperture having a first end 122A and a second end 124A. The first end 122A comprises a first width, and can be sized and dimensioned to readily receive cord 128 and a cord block (not shown). The second end 124A comprises a second width smaller than the first width, and can be sized and dimensioned to receive cord 128, but not cord block, which has a larger width or diameter than cord 128. The second end 124A can advantageously include a catch 126A that keeps cord 128 from moving towards the first end, and the first and second ends can be connected via a U-shaped or otherwise curved portion that further prevents the cord from inadvertently being moved from the second end to the first end.

It is contemplated that the first width of the first end 122A can be larger than, equal to, or even smaller than a diameter or width of cord block. Where the first width is smaller than a diameter or width of the cord block, the cord block can still be readily received by first end where the cord block is compressible. Similarly, the second width of the second end 124A can be smaller than a diameter or width of the cord block (even when compressed), but be larger than, equal to, or even smaller than a diameter or width of cord 128. Where the second width is smaller than a diameter or width of cord 128, the cord 128 can still be readily received by second end where cord 128 is compressible. It is contemplated that the first width can be determined as a function of a diameter or width of a cord block, and that the second width can be determined as a function of a diameter or width of a cord.

A tightening system of the inventive subject matter can advantageously have a varying thickness, which can provide for a varying flexibility throughout the length or width of the housing. For example, housing 100A includes thickened areas 108A and 108B, which are thicker than thinned areas (e.g., 102A). Thickened area 108A is positioned between retention device 120A and lobe 112A, and thickened area 108B is positioned between lobe 112A and lobe 112B. Housing 100A also includes a thinned area 102A or recessed portion along its length that has an overall height that is less than a normal height of the housing 100A, or thickened areas 108A and 108B. This advantageously allows for the housing 100A to be attached to a fabric brace or other orthotic, for example, by sewing or the use of other fasteners.

Similarly to apertures at ends 106A and 106B, thinned area 102A can also provide for areas of greater flexibility relative to other portions of housing 100A such as thickened areas 108A and 108B. The thinned area 102A preferably include recessed paths (e.g., 104A) that lead to an opening in a corresponding lobe (e.g., 112A) along which a sheave 110A (including pin 114A) can be inserted into the lobe. Once a sheave is slid into or under a lobe via a recessed path, the sheave's pin can be snap fit or otherwise positioned in, and rotatably secured between a lobe and the housing's top surface such that an inadvertent removal of the sheave is prevented. For example, the sheave can be secured in place such that the position of the pins do not move relative to the lobe and housing's top surface, but a rotation of the sheave, including the pin(s), in one or more directions can occur.

Figure 3A:
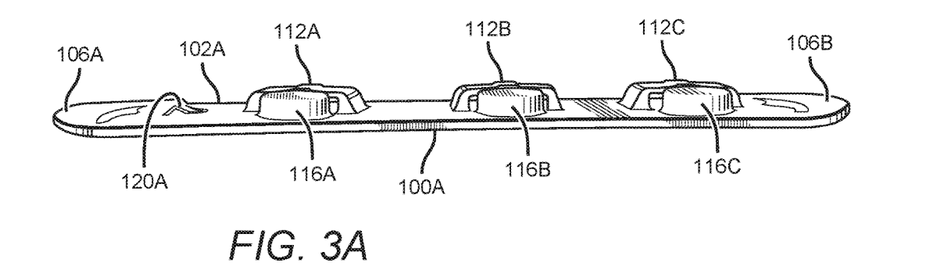
FIGS. 3A-3D are various side views of the tightening system of FIG. 1A without sheaves.
Figure 3B:
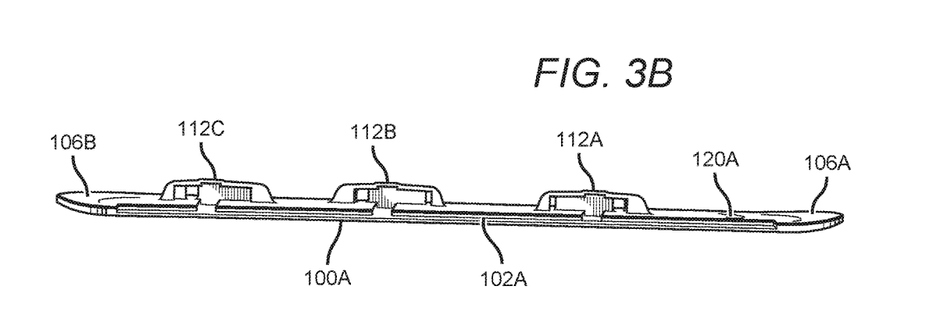

As best seen in FIGS. 3A and 3B, the first piece of the lobe could comprise a raised path that is sized and dimensioned to guide a pin that extends from a first wall (top surface) of a sheave. As illustrated in FIG. 1A, the top surface of housing 100A can include through-holes (or recessed portions) positioned between first and second pieces or portions of a lobe in which a pin that extends from a second wall (bottom surface) of a sheave can be rotatably secured. As seen in FIG. 2B, the pin that extends from the first wall is at least partially positioned, and rotatably secured in a gap between first and second pieces or portions of a lobe, and the pin that extends from the second wall of the sheave is at least partially positioned, and rotatably secured in a through-hole of the top surface that aligns with a central portion of the gap.

FIGS. 3A-3E are various side views of the tightening system of FIG. 1A with sheaves 110A, 110B, and 110C removed.

FIG. 3A illustrates a view from the thicker side edge of housing 100A that does not include a thinned area 102A. Blocking elements 116A, 116B, and 116C are positioned adjacent the thicker side edge, and lobes 112A, 112B, and 112C are positioned between blocking elements 116A, 116B, and 116C and thinned area 102A. FIG. 3B illustrates a view from the side edge of housing 100A including thinned area 102A from which sheaves 110A, 110B, and 110C can be inserted through openings defined by the lobes and top surface. Thinned area 102A includes paths (e.g., 104C) for sheave pins, as more clearly illustrated in FIG. 3D. Lobes 112A, 112B, and 112C each include raised paths that vertically align with the recessed paths to receive pins of the sheaves.

When a sheave is inserted through an opening between a lobe (e.g., lobe 112C) and the top surface, the sheave's pins or pin portions can cause lobe 112C to slightly flex upwards. When the sheave is secured in place between the lobe and the top surface, the lobe can return to its original shape. Additionally or alternatively, the raised path (or recessed path of a top surface) could be tapered, such that the sheaves are readily inserted through the opening, causing the lobe or other portion of the housing to flex, but not readily removable (without tools, damage, or breakage) once secured.

Figure 3C:
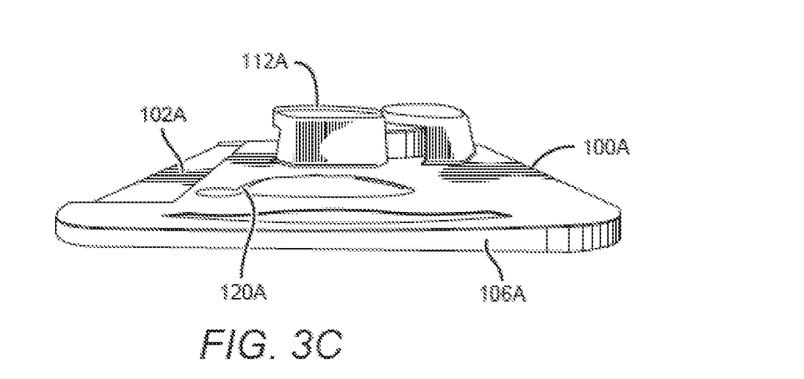
Figure 3D:
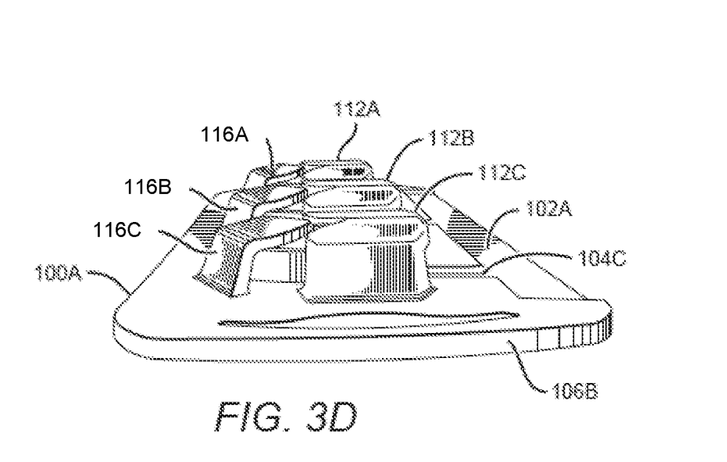
Figure 3E:
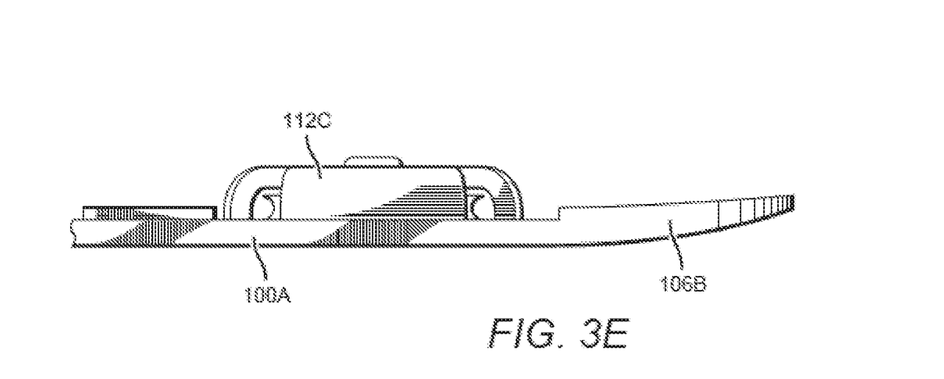
FIG. 3E is a side view of a portion of the tightening system of FIG. 1A.

FIG. 3C shows a side view from end 106A, and illustrates that end 106A can be slightly raised or curved upward relative to a central portion of housing 100A (between ends 106A and 106B). FIG. 3C also illustrates that cord retention device 120A can be raised or bulged relative to the central portion of the housing 100A, which can assist in aligning a distance between cord 128 and housing 100A at cord retention device 120A with a distance between cord 128 and housing 100A when positioned in a cord receiving portion (e.g., 111A) of a sheave (e.g., 110A). The raised configuration of the cord retention device 120A also provides an area for the cord block (e.g., knot) to be positioned beneath the housing without creating a bulge. FIG. 3D is a side view from end 106B, and similarly illustrates that end 106B can be raised or curved upward relative to a central portion of housing 100A. The raised ends can advantageously reduce the possibility of a sharp end causing discomfort to the wearer of a brace or other object comprising housing 100A. FIG. 3E is an enlarged partial view from the thicker long side edge of housing 100A as in FIG. 3A more clearly showing raised end 106B.

FIG. 4 illustrates a tightening system including two housings between which one or more cords and an optional connecting material can extend. Housing 100A includes first end 106A, second end 106B, cord retention device 120A, thinned area 102A, lobes 112A, 112B and 112C, blocking elements 116A, 116B and 116C, and sheaves 110A, 110B and 110C having pins 114A, 114B and 114C, respectively. Housing 100B includes first end 106C, second end 106D, cord retention device 120B, thinned area 102B, lobes 112E, 112F and 112G, blocking elements 116E, 116F and 116G, and sheaves 110E, 110F and 110G having pins 114E, 114F and 114G, respectively.

It should be appreciated that in FIG. 4, housing 100B is identical to housing 100A, but rotated 180 degrees such that the blocking elements 116A-C face blocking elements 116E-F. However, it is contemplated that two housings used on a brace or other object do not need to be identical and could, for example, include different numbers of lobes and sheaves, or longer and shorter end portions.

Cord 128 is coupled with cord retention device 120B, and includes a knot or other block that prevents a first end of cord 128 from passing through the narrower end or catch of the cord retention device (or track) 120B. The free portion of cord 128 can then pass through a gap or opening of lobe 112C on a first side of blocking element 116C, and be positioned at least partially within the cord receiving portion of sheave 110C. Cord 128 could pass through the gap or an opening of lobe 112C on a second and opposite side of blocking element 116C, and enter lobe 112E through an opening on a first side of blocking element 116E. Cord 128 then could be positioned at least partially within the cord receiving portion of sheave 110E, and pass through a gap or an opening of lobe 112E on a second opposite side of blocking element 116E. Cord 128 could then pass through the gap or an opening of lobe 112B on a first side of blocking element 116B, be positioned at least partially within the cord receiving portion of sheave 110B, and pass through the gap or an opening of lobe 112B on a second side of blocking element 116B.

When the tightening system of FIG. 4 is used with, for example, a lower back brace, a user can pull cord 128 in a first direction to shorten the distance between end 106B and end 106C of housings 100A and 100B. In some embodiments, sheaves 110C, 110E and 110B can be configured to rotate within their respective lobes when cord 128 is pulled or released. In some embodiments, sheaves 110C, 110E and 110B can be configured as non-rotating sheaves.

It should be appreciated that cord 128 could be coupled with one or more other sheaves of housings 100A or 100B. For example, cord 128 could be coupled with each of the sheaves of housings 100A and 100B. It should also be appreciated that a second cord could be coupled with retention device 120A, and at least partially positioned within sheaves 110G, 110A 110F. The second cord could be pulled by a user of the lower back brace in a second direction, which could be an opposite direction of cord 128, and a distance between ends 106A and 106D can be shortened.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A tightening system, comprising:
a housing having a top surface;
a set of lobes positioned on the top surface, and including a first lobe;
wherein a first portion of the top surface includes a recessed path, and wherein the first lobe and the first portion form an opening that is sized and dimensioned to receive a first sheave; and
wherein the first sheave is configured to be rotatably secured at least partially between the first lobe and the first portion.

2. The tightening system of claim 1, wherein the top surface of the housing comprises a thinned region that extends along at least 50% of a length of the housing.

3. The tightening system of claim 2, wherein the thinned region extends along at least 25% of an outer edge of the housing.

4. The tightening system of claim 3, wherein the thinned region includes the recessed path.

5. The tightening system of claim 1, wherein the first sheave comprises a first pin sized and dimensioned to at least partially be positioned within the recessed path.

6. The tightening system of claim 5, wherein the first lobe comprises first and second pieces that are separated by a gap, and wherein the gap is sized and dimensioned to receive at least a portion of the first pin.

7. The tightening system of claim 1, wherein the first lobe comprises a blocking member.

8. The tightening system of claim 7, wherein the first lobe and blocking member comprises a single piece.

9. The tightening system of claim 8, wherein the single piece comprises an aperture sized and dimensioned to receive a first cord.

10. The tightening system of claim 1, wherein the housing comprises first and second ends connected by left and right sides, and wherein the first and second ends are curved upwardly with respect to a mid-portion of the housing.

11. The tightening system of claim 1, further comprising a cord configured to wrap at least partially about one or more of the sheaves.

12. The tightening system of claim 1, further comprising:
a second housing having a second top surface;
a second set of lobes positioned on the second top surface, and including a second lobe;
wherein a first portion of the second top surface includes a second recessed path, and wherein the second lobe and the first portion of the second top surface form an opening that is sized and dimensioned to receive a second sheave; and
wherein the second sheave is configured to be rotatably secured at least partially between the second lobe and the first portion of the second top surface.

13. The tightening system of claim 12, further comprising a cord configured to wrap at least partially about the first and second sheaves.

14. The tightening system of claim 1, wherein the second lobe includes a second block that is configured to block the second sheave from moving in a first direction.

15. The tightening system of claim 14, wherein the second sheave comprises a second pin that extends from a first wall of the second sheave, and wherein the second lobe includes a first receiver sized and dimensioned to receive and lock the second pin.

16. The tightening system of claim 15, wherein the first receiver is at least one of a raised path and a through-hole.

17. The tightening system of claim 15, wherein the second pin extends from a second wall of the second sheave, and wherein the second top surface comprises a through-hole positioned directly below the first receiver, and sized and dimensioned to receive at least a portion of the second pin.

18. The tightening system of claim 15, wherein the second pin includes a first pin portion that extends from the first wall of the second sheave, and a second pin portion that extends from a second wall of the second sheave, and wherein the second top surface comprises at least one of a recess and a through-hole positioned directly below the first receiver, and sized and dimensioned to receive at least a portion of the second pin portion.

19. The tightening system of claim 1, wherein the first sheave comprises a pin, and wherein the first lobe comprises a recessed path sized and dimensioned to receive at least a portion of the pin.

20. The tightening system of claim 19, wherein a raised path is tapered.

21. A housing for a pulley system, comprising:
a top surface and a bottom surface;
a set of lobes positioned on the top surface; and
a set of sheaves,
wherein each sheave of the set of sheaves is configured to be inserted into and rotatably mounted within at least one lobe of the set of lobes and
wherein at least one of the top surface and the bottom surface comprises a thinned region along one side configured for attachment to a brace or orthotic.

22. The housing of claim 21, wherein the housing comprises first and second ends connected by left and right sides, and wherein the first and second ends are curved upwardly with respect to a central portion of the housing.

23. A lower back brace, comprising:
a belt configured to wrap around a mid-portion of a wearer;
a tightening system coupled to the belt and comprising:
a first housing having a first top surface;
a second housing having a second top surface;
a cord extending between the first and second housings; and
a set of lobes positioned on the first top surface, and including a first lobe; and
wherein a first portion of the first top surface includes a recessed path, and wherein the first lobe and the first portion form an opening that is sized and dimensioned to receive a first sheave; and
wherein the first sheave is configured to be rotatably secured at least partially between the first lobe and the first portion; and
wherein pulling the cord in a first direction shortens a distance between at least a portion of the first housing and at least a portion of the second housing.

24. The lower back brace of claim 23, wherein the belt comprises a connector material, and wherein the first and second housings are coupled to first and second sides of the connector material.

* * * * *